United States Patent [19]

Koch et al.

[11] Patent Number: 4,685,459

[45] Date of Patent: Aug. 11, 1987

[54] DEVICE FOR BIPOLAR HIGH-FREQUENCY COAGULATION OF BIOLOGICAL TISSUE

[75] Inventors: Rainer Koch; Rüdiger Stockert, both of Freiburg, Fed. Rep. of Germany

[73] Assignee: Fischer MET GmbH, Freiburg, Fed. Rep. of Germany

[21] Appl. No.: 836,968

[22] Filed: Mar. 6, 1986

[30] Foreign Application Priority Data

Mar. 27, 1985 [DE] Fed. Rep. of Germany ....... 3511107

[51] Int. Cl.⁴ ............................................ A61B 17/39
[52] U.S. Cl. ............................... 128/303.17; 219/234; 219/241
[58] Field of Search ........... 128/303.1, 303.13–303.17, 128/736; 219/230, 233, 234, 241

[56] References Cited

U.S. PATENT DOCUMENTS

| | | | |
|---|---|---|---|
| 2,596,933 | 5/1952 | Kirk | 219/241 |
| 3,980,861 | 9/1976 | Fukunaga | 219/230 |
| 4,074,719 | 2/1978 | Semm | 128/303.1 |
| 4,322,594 | 3/1982 | Brisson | 128/736 X |
| 4,531,524 | 7/1985 | Mioduski | 128/303.13 X |

OTHER PUBLICATIONS

Sugita et al., "Bipolar Coagulator . . . ", J. Neurosurg, vol. 41, Dec. 1974, pp. 777–779.

Primary Examiner—Lee S. Cohen
Attorney, Agent, or Firm—Jeffers, Hoffman & Niewyk

[57] ABSTRACT

A device for bipolar high-frequency coagulation of biological tissue between two contact faces of a coagulating instrument. The two contact faces are connected to an output of a high-frequency generator. A temperature sensor is arranged near each of the two contact faces. A circuit for evaluating the measured temperatures and/or the temperature differential controls the coagulation temperature and the shutoff of the high-frequency generator as a preselected temperature or temperature differential is exceeded. Moreover, an indicating device is provided for acoustically and/or optically indicating the temperatures on the contact faces as well as the temperature differential between the contact faces.

23 Claims, 3 Drawing Figures

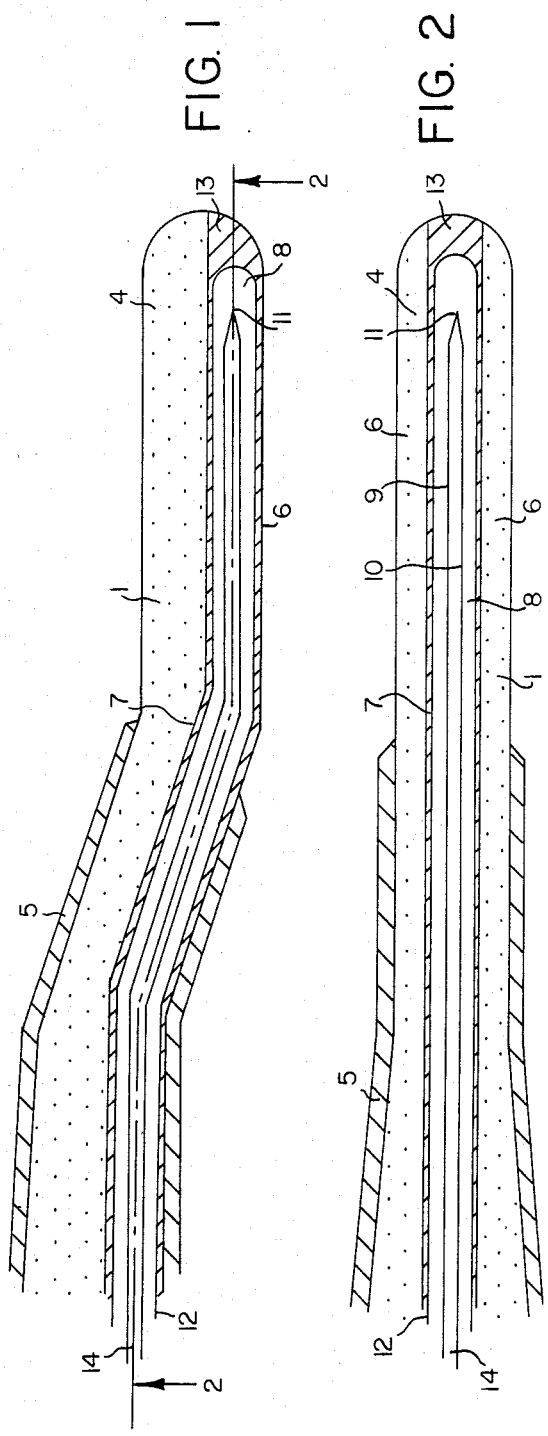

DEVICE FOR BIPOLAR HIGH-FREQUENCY COAGULATION OF BIOLOGICAL TISSUE

BACKGROUND OF THE INVENTION

This invention concerns a device for bipolar high-frequency coagulation of biological tissue accomplished between two contact faces of a coagulating instrument which are connected to the output of a controllable high-frequency generator.

Such devices have been previously known in surgery, for instance, in bipolar coagulation pincers. However, due to uneven current densities at varying contact conditions and because the high-frequency supply does not vary in response to the tissue temperature which has already been reached, burns occur easily with the prior devices. This is because a very high temperature may occur on one of the two pincer tips although the other pincer tip may still be relatively cool.

SUMMARY OF THE INVENTION

Based upon the above-described state of prior art, the object of the invention is to provide a device which makes it possible to perform bipolar high-frequency coagulations, without the danger of causing burns and without the danger of exceeding the preselected coagulation temperature.

This problem is solved by the present invention by providing temperature sensors which are arranged near the two contact faces of the coagulating instrument. The sensors are connected to circuitry capable of evaluating the measured temperatures and/or temperature differences.

In a suitable embodiment, encased thermocouples are embedded, as thermosensors, in the shank tips of coagulating pincers. The temperature sensor signals pass through a DC voltage bridging amplifier to a differential amplifier whose output signal can activate both an indicating unit and a circuit which makes it possible to switch off the high-frequency generator during the presence of harmless tissue temperatures and prior to a preselected temperature differential being exceeded. The temperature sensor signals, are, thus, utilized with the aid of a comparator, a changeover switch, and a controller, to provide temperature-controlled coagulation at a constant temperature between the two instrument shanks. This is done by controlling the output of the high-frequency generator which is connected to the instrument shanks.

BRIEF DESCRIPTION OF THE DRAWINGS

The above-mentioned and other features and objects of this invention and the manner of obtaining them will become more apparent and the invention itself will be better understood by reference to the following description of an embodiment of the invention taken in conjunction with the accompanying drawings wherein:

FIG. 1 is a longitudinal cross-sectional view showing the front end of a shank of the coagulating pincers according to a preferred embodiment of the present invention;

FIG. 2 is a cross-sectional view taken along line II—II of FIG. 1; and

Corresponding reference characters indicate corresponding parts throughout the several views of the drawings.

Figure 3:
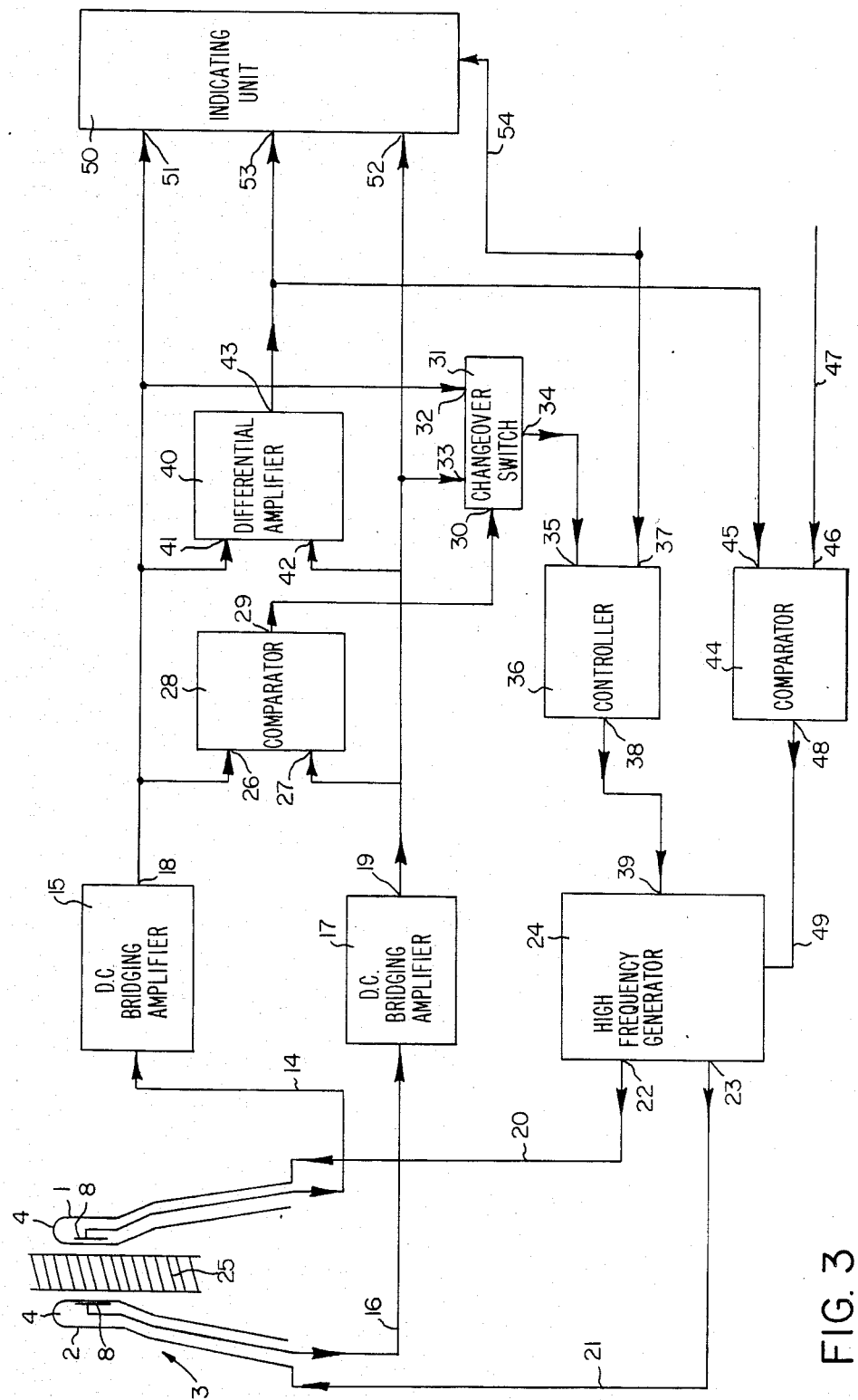
FIG. 3 is a schematic diagram of a circuit for the evaluation of the detected temperatures and/or temperature differentials with the aid of the coagulation pincers.

The exemplifications set out herein illustrate a preferred embodiment of the invention in one form thereof and such exemplifications are not to be construed as limiting the scope of the disclosure or the scope of the invention in any manner.

DETAILED DESCRIPTION OF THE PREFERRED EMBODIMENT

In FIGS. 1 and 2, there is shown the front end of one of shanks 1 and 2 of the coagulating pincers 3. Pincers 3 are also shown schematically in FIG. 3, in an enlarged cross section.

FIG. 1 shows a cross section of the forward end of shank 1 of the coagulating pincers 3 parallel to the plane within which shanks 1 and 2 move when the coagulating pincers are operated, and FIG. 2 shows a cross-sectional plan view of shank 1 along line II—II, in the direction of movement.

Referring to FIGS. 1 and 2, shanks 1 and 2 are coated with an insulating enamel 5 up to a point near shank tips 4 in a manner customary with coagulating pincers. Shanks 1 and 2 are made of a suitable material such as an electrically conductive metal through which high-frequency current is passed to contact faces 6 on the insides near shank tips 4.

Provided on the inside of shanks 1 and 2 are grooves 7 which originate from tips 4 of shanks 1 and 2. In the embodiment illustrated in FIGS. 1 and 2, grooves 7 serve to receive an encased thermocouple 8 consisting essentially of an NiCr wire 9 and Ni wire 10 which are soldered or welded together at their front ends for forming a temperature measuring junction 11. As shown in the drawings, temperature measuring junction 11 is located opposite each contact face 6 of shanks 1 and 2, and is set back inside a tubular shell 12 which is filled with quartz sand.

Tubular shell 12 is embedded in groove 7 by filling the remaining spaces with brazing solder and, thus, sealing machined groove 7. After insertion of the shell type thermocouple 8, any protruding brazing solder is removed by grinding so as to restore the original shape of shanks 1 and 2.

The temperature measuring junction 11, which in the embodiment according to FIGS. 1 and 2 is realized with the aid of a shell type thermocouple 8, may be replaced as well by other temperature sensors having sufficiently small geometric dimensions and a sufficiently short response time. For instance, a thermal resistor type PT 100 may be used and installed in shanks 1 and 2 in a similar fashion as shown in FIGS. 1 and 2.

The thermovoltage produced by thermocouple 8 in shank 1 proceeds through leads 14 to a first DC voltage bridging amplifier 15 as illustrated in FIG. 3. Bridging amplifier 15 includes a high-frequency filter for filtering out the high-frequency current needed and utilized for coagulating.

Second shank 2 of coagulating pincers 3, is connected through line 16 to a second DC bridging amplifier 17 which has the same characteristics as the first DC bridging amplifier 15. Thus, the signals provided on outputs 18 and 19 of DC bridging amplifiers 15 and 17, respectively, are a function of and depend on the current of thermocouples 8 which in turn depend on and are a function of the temperature on tips 4 of shanks 1 and 2.

As shown further in FIG. 3, shanks 1 and 2 are connected through feed lines 20 and 21 with the high frequency outputs 22 and 23, respectively, of high-frequency generator 24 generating, for example, a coagulating current with a frequency of 450 kHz. High-frequency generator 24 is activated, as commonly known, by a sensor circuit or a foot switch, which are not illustrated in FIG. 3.

Once shanks 1 and 2 touch biological tissue 25 with their contact faces 6, as illustrated schematically in FIG. 3, and the high-frequency generator 24 is turned on, biological tissue 25 is heated and coagulation takes place commencing at a sufficiently high temperature. Due to uneven current densities at varying contact conditions, varying temperatures on shanks 1 and 2 are created. The device recognizes temperature differentials in the uncritical range and shuts the high-frequency generator 24 off when a preset temperature differential occurs. Coagulation can be restarted upon proper change of the contact conditions and changed reapplication of coagulating pincers 3.

The respective temperatures of contact faces 6 of coagulation pincers 3 are monitored with the aid of the shell type thermocouples 8 which are transmitted, by way of outputs 18 and 19, as electrical signals to inputs 26 and 27, respectively, of first comparator 28. Output 29 of comparator 28 is connected with input 30 of a changeover switch 31 for processing the temperature information occurring on outputs 18 and 19. Depending on the output signal of the comparator 28, either the temperature signal of first shank 1 occurring on input 32 of the changeover switch 31 or the temperature signal of second shank 2 occurring on input 33 of the changeover switch 31 proceeds to output 34 of the changeover switch 31. The signal at output 34 of switch 31 is, thus, a measure of and corresponds with the higher one of the two coagulation temperatures of shanks 1 or 2.

To safely prevent the coagulation temperature from being exceeded, output 34 is connected with the input 35 of a controller 36 whose set value input 37 carries a reference signal which determines the desired or preselected coagulation temperature as a temperature set value. Thus, after an even temperature rise at ends 4, temperature-controlled coagulation at a constant temperature is brought about through output 38 of the controller 36 and controlled input 39 of high-frequency generator 24.

To recognize temperature differentials between shanks 1 and 2 of coagulating pincers 3 during the initial phase of the coagulation and to shut off high-frequency generator 24 before tissue 25 burns can occur, the difference between the temperatures of contact faces 6 is additionally assessed. Provided for this purpose is a differential amplifier 40 whose differential inputs 41 and 42 are connected to outputs 18 and 19 of DC bridging amplifiers 15 and 17, respectively. An output signal occurs at output 43 of differential amplifier 40 whose level depends on the absolute difference between the two temperatures of shanks 1 and 2. If tissue 25, located between contact faces 6, is, upon activation of high-frequency generator 24, unevenly heated because of uneven contact conditions and current densities, high-frequency generator is shut off with the aid of second comparator 44. Output 43 of differential amplifier 40 is connected, for that purpose, with monitoring input 45 of comparator 44. Set value input 46 of comparator 44 receives, by way of a line 47, a voltage which determines the cutout value of the temperature differential. If the electrical signal occurring on the monitoring input 45 is higher than the signal occurring on the set value input 46, output 48 of the comparator 44 transmits, via a shutoff line 49, a shutoff signal to high-frequency generator 24 thereby reliably preventing excessive temperature differences.

As can additionally be seen in FIG. 3, the evaluating and control circuit comprises, in addition to a controller 36 ensuring a constant coagulation at the temperature preselected as the set value and comparator 44 for shutting off high-frequency generator 24 at temperatures exceeding a preselected value, an indicating unit 50 for indicating the temperatures on the two shanks 1 and 2 and the temperature difference between shanks 1 and 2. Indicating unit 50 can be an acoustic, optical or an acoustically and optically effective device. Indicating unit 50 comprises two temperature inputs 51 and 52 which are connected with outputs 18 and 19 of the DC voltage bridging amplifiers 15 and 17, respectively. Moreover, indicating unit 50 has a temperature differential input 53 which is connected with differential output 43 of differential amplifier 40.

In the case of an acoustic indicating unit 50, the temperature signals and the temperature differential signals can be passed acoustically to the operator, for instance, by variation of the loudness, frequency or the clock of a chopped sound. In the case of an optical type of indicating unit 50, a display may take place by the variation of the brightness, the color, or the flicker frequency at which a light-emitting element turns on and off. The change of the acoustic indicating signal is suitably the strongest near the set value so as to enable an indication as sensitive as possible in the range of particular interest. Therefore, indicating unit 50 carries, via a signal line 54, the same voltage signal as the set value input 37 which represents the desired coagulation temperature. For indication of the temperature differential, the set value by which the indication changes the strongest is preferably a temperature differential having a value of zero.

While the invention has been described as having a specific embodiment, it will be understood that it is capable of further modification. This application is therefore intended to cover any variations, uses or adaptations of the invention following the general principles thereof and including such departures from the present disclosure as come within known or customary practice in the art to which this invention pertains and fall within the limits of the appended claims.

What is claimed is:

1. A device for bipolar high-frequency coagulation of biological tissue comprising:
   a coagulating pincer with a first shank defining a first contact face and a second shank defining a second contact face;
   a controllable high-frequency generator;
   said first shank contact fee and said second shank contact face electrically connected to said generator;
   a pair of temperature sensors, one of said sensors located near said first shank contact face and the other of said sensors located near said shank contact face;
   evaluation means having a controller for controlling said high-frequency generator with a first selectively preset input representing a predetermined coagulation temperature and a second input;
   a first comparator connected to said temperature sensors, and having an output; and changeover switch means having a first input connected to said output of said first comparator, a second input connected to one of said temperature sensors, a third input connected to the other of said temperature sensors, and an output connected to said second input of said controller, whereby said changeover switch means electrically connects the temperature sensor representing the highest temperature to said second input of said controller;

said evaluation means connected to said temperature sensors for evaluating the temperatures near said first and second contact faces and controlling said high-frequency generator in response to said highest temperature.

2. The device according to claim 1 wherein said first shank defines a first shank tip and said second shank defines a second shank tip, wherein said first and second contact faces are, respectively, located on said shank tips and said temperature sensors are embedded in said shank tips.

3. The device according to claim 2 wherein said temperature sensors are encased thermacouples which extend into said first and second shank tips.

4. The device according to claim 3 wherein each of said temperature sensors is a connection junction of an NiCrNi encased thermoelement.

5. The device according to claim 3 wherein said first and second shanks of said coagulating pincers comprise longitudinal grooves, said grooves originating from the inside of each of said first and second contact faces facing one another and extending up into said first and second shank tips, said encased thermocouples embedded within said grooves by hard solder.

6. The device according to claim 1 wherein said temperature sensors are resistance elements with a positive temperature coefficient.

7. The device according to claim 1 wherein said evaluation means further comprises a differential amplifier having two inputs and an output, said inputs respectively connected to said pair of temperature sensors, and a second comparator having a first input connected to said output of said differential amplifier, a second input connected to a selectively preset input representing a cutout temperature difference, and an output connected to said high frequency generator for switching off said generator when said selectively preset cutout temperature difference is exceeded.

8. The device according to claim 7 further comprising
an acoustic indicating unit connected to said ouput of said differential amplifier.

9. The device according to claim 8 wherein, said indicating unit includes means for varying one of a sound frequency and loudness in response to the output from said differential amplifier and wherein the variation variable is strongest in the vicinity of a preset value.

10. The device according to claim 7 further comprising
an optical indicating unit connected to said output of said differential amplifier.

11. The device according to claim 10 wherein, said indicating unit includes means for varying one of a flicker frequency, brightness and color in response to the output from said differential amplifier and wherein the variation variable is strongest in the vicinity of a preset value.

12. The device according to claim 7 further comprising
an optical and acoustic indicating unit connected to said output of said differential amplifier.

13. The device according to claim 12 wherein, said indicating unit includes means for varying one of a sound frequency, flicker frequency, loudness, brightness and color in response to the output of said differential amplifier and wherein the variation variable is strongest in the vicinity of a preset value.

14. The device according to claim 1 further comprising an optical indicating means connected to said temperature sensors forindicating the temperatures on said contact faces.

15. The device according to claim 14 wherein, said indicating means includes means for varying one of a flicker frequency, brightness and color in response to the temperatures on said contact faces and wherein the variation variable is strongest in the vicinity of a preset value.

16. The device according to claim 1 further comprising an acoustic indicating means connected to said temperature sensors for indicating the temperatures on said contact faces.

17. The device according to claim 16 wherein, said indicating means includes means for varying one of a sound frequency and loudness in response to the temperatures on said contact faces and wherein the variation variable is strongest in the vicinity of a preset value.

18. The device according to claim 1 further comprising an acoustic and optical indicating means connected to said temperature sensors for indicating the temperatures on said contact faces.

19. The device according to claim 18, wherein, said indicating means includes means for varying one of a sound frequency, flicker frequency, loudness, brightness and color in response to the temperature on said contact faces and wherein the variation variable is strongest in the vicinity of a preset value.

20. A device for bipolar high-frequency coagulation of biological tissue comprising;
a coagulating pincer with a first shank defining a first contact face and a second shank defining a second contact face;
a controllable high-frequency generator;
said first shank contact face and said second shank contact face electrically connected to said generator;
a pair of temperature sensors, one of said pair of sensors located near said first shank contact face and the other of said sensors located near said second shank contact face;
a control means having a controller with a first and second input and an output, said first input connected to a selectively preset electrical signal representing a predetermined coagulation temperature, said output connected to said high-frequency generator
a first comparator connected to said temperature sensors and having an output; and
changeover switch means having a first input connected to said output of said first comparator, a second input connected to one of said temperature sensors, a third input connected to the other of said temperature sensors, and an output connected to said second input of said controller, whereby said changeover switch means electrically connects the temperature sensor representing the highest temperature to said second input of said controller;

said control means connected to said temperature sensors for evaluating the temperatures near said contact faces and controlling said high-frequency generator in response to the temperatures sensed by said sensors.

21. The device according to claim 20 wherein said first shank defines a first shank tip and said second shank defines a second shank tip, wherein said first and second contact faces are, respectively, located on said first and second shank tips and said temperature sensors are encased thermocouples embedded in said shank tips.

22. The device according to claim 20 wherein said control means comprises a differential amplifier having an input and an output, said input connected to said temperature sensors, and a second comparator having a first input connected to said output of said differential amplifier, a second input connected to a selectively preset input representing a temperature difference, and an output connected to said high-frequency generator, said control means independently switching off said generator when said selectively preset temperature difference is exceeded.

23. A device for bipolar high-frequency coagulation of biological tissue comprising;
   a coagulating pincer with a first shank defining a first contact face and a second shank defining a second contact face;
   a controllable high-frequency generator;
   said first shank contact face and said second shank contact face electrically connected to said generator;
   a pair of temperature sensors, one of said pair of sensors located near said first shank contact face and the other of said sensors located near said second shank contact face;
   control means for connecting the highest temperature of one of said first contact face and said second contact face to said generator,
   means for sensing the temperature differential between said first contact face sensor and said second contact face sensor;
   said control means for connecting the highest temperature contact face and said means for sensing the temperature differential coupled between said temperature sensors and said generator to control the energization of said pincer.

* * * * *

UNITED STATES PATENT AND TRADEMARK OFFICE
CERTIFICATE OF CORRECTION

PATENT NO. : 4,685,459

DATED : August 11, 1987

INVENTOR(S) : Rainer Koch

It is certified that error appears in the above-identified patent and that said Letters Patent is hereby corrected as shown below:

Claim 1, Col. 4, line 56, change "fee" to --face--.

Signed and Sealed this

Twenty-fourth Day of November, 1987

Attest:

DONALD J. QUIGG

Attesting Officer

Commissioner of Patents and Trademarks